United States Patent [19]
Lamuraglia

[11] Patent Number: 5,824,080
[45] Date of Patent: Oct. 20, 1998

[54] PHOTOCHEMISTRY FOR THE PREPARATION OF BIOLOGIC GRAFTS— ALLOGRAFTS AND XENOGRAFTS

[75] Inventor: Glenn M. Lamuraglia, Winchester, Mass.

[73] Assignee: The General Hospital Corporation, Boston, Mass.

[21] Appl. No.: 708,376

[22] Filed: Sep. 4, 1996

Related U.S. Application Data

[60] Provisional application No. 60/004,480 Sep. 28, 1995.
[51] Int. Cl.$^6$ .................................................. A61F 2/02
[52] U.S. Cl. .................................................. 623/11
[58] Field of Search ............................. 623/1, 2, 11, 12, 623/66; 435/240.23; 128/898; 604/21

[56] References Cited

U.S. PATENT DOCUMENTS

| | | | |
|---|---|---|---|
| 5,015,584 | 5/1991 | Brysk .................................. | 435/240.23 |
| 5,192,312 | 3/1993 | Orton .................................. | 623/2 |
| 5,200,400 | 4/1993 | Teramoto et al. ................... | 514/45 |
| 5,298,018 | 3/1994 | Narciso, Jr. ......................... | 604/21 |

OTHER PUBLICATIONS

Grant et al., "Photodynamic therapy of normal rat arteries after photosensitisation using disulphonated aluminum phthalocynanine and 5–aminolaevulinic acid", *Br. J. Cancer* 70:72–78, (1994).

Henderson et al., "How Does Photodynamic Therapy Work?", (1992), *Photochemistry and Photobiology*, 55:145–157, (1992).

LaMuraglia et al., "Cloroaluminum Sulfonated Phthalocyanine Partitioning in Normal and Intimal Hyperplastic Artery in the Rat", *Amer. J. of Pathology*, 142:1898–1900, (1993).

LaMuraglia et al., "Photodynamic therapy inhibition of experimental intimal hyperplasia: Acute chronic effects", *J. of Vascular Surgery*, 19:322–331, (Feb. 1994).

Marin et al., "Immunomodulation of vascular endothelium: Effects of ultraviolet B irradiation on vein allograft rejection", *J. of Vascular Surgery*, 11:103–111, (1990).

Ortu et al., Photodynamic Therapy of Arteries, A Novel Approach for Treatment of Experimental Intimal Hyperplasia, *Circulation*, 85:1189–1196, (1992).

Verweij et al., "Photodynamic Protein Cross–Linking", *Biochimica et Biophysica Acta*, 647:87–94, (1981).

Copy of PCT Search Report for PCT/US96/15404.

*Primary Examiner*—David Isabella
*Attorney, Agent, or Firm*—Fish & Richardson P.C.

[57] ABSTRACT

Photodynamic therapy (PDT), a technique to produce cytotoxic free radicals, was used to prepare arterial allografts. After impregnation with the photo-sensitizer chloroaluminum sulfonated phthalocyanine, aortas of ACI rats were PDT-treated and transplanted in Lewis rats. PDT grafts were completely reendothelialized by 4 weeks.

7 Claims, No Drawings

PHOTOCHEMISTRY FOR THE PREPARATION OF BIOLOGIC GRAFTS— ALLOGRAFTS AND XENOGRAFTS

CROSS-REFERENCE TO RELATED APPLICATION

This application claims priority from provisional application Ser. No. 60/004,480, filed Sep. 28, 1995.

This invention relates to methods and materials for reducing or inhibiting the rejection of arterial allografts and other grafts.

Biological vascular allografts have proven less than satisfactory because of thrombosis and aneurysmal degeneration during chronic rejection.

It is widely accepted that autologous artery or vein is the gold standard for small diameter arterial reconstruction, and no other graft rivals their patency performance. Fogle M A, Whittemore A D, Couch W P, Mannick J A, A comparison of in situ and reversed saphenous vein grafts for infrainguinal reconstruction, J. Vasc Surg. 1987, 5:46–52; Taylor L M, Edwards J M, Porter J M, Present status of reversed vein bypass: Five-year results of a modem series, J. Vasc Surg. 1990, 11:193–205. Since autologous grafts are not always available, interest in bioprostheses from allo- and xenografts has periodically resurfaced over the past years. DeBakey M E and Creech O. Jr., Occlusive disease of the aorta and its treatment by resection and homograft replacement, Ann Surg. 1954, 140:290–310; Szilagyi D E, McDonald R T, Smith R F, Whitcomb J G., Biologic fate of human arterial homografts, Arch Surg. 1957, 75:506–529; Szilagyi D E, Overhulse P R, Logrippo G A, Use of chemically sterilized arterial homografts, Clin Res. Proc. 1954, 2:108–113. In fact, it was an aortic homograft that was used for the first surgical treatment of abdominal aortic aneurysms. Dubost C, Allary M, Oeconomos N, A propos du tratement des aneurysmes de l'aorte-ablation de l'aneurysme: retablissement de la continuite par greffe de l'aorte humaine conservee. Mem Acad Chir (Paris), 1951, 77:381–383. However, thus far viable exogenous tissue has been unsuitable for safe, long-term, arterial replacement because of the associated chronic rejection process which can lead to graft dilatation, rupture, or occlusion.

Endothelial and vascular smooth muscle cells are probably the main antigenic targets in immunological arterial wall remodeling. Mennander A, Tiisala S, Halttunen J, Yilmaz S, Paavonen T, Havry P, Chronic rejection in rat aortic allografts: an experimental model for transplant arteriosclerosis, Arterioscler Thromb. 1991, 11:671–680; Dumont C E, Plissonier D, Guettier C, Michel J B, Effects of glutaraldehyde on experimental arterial iso- and allografts in rats, J Surg Res. 1993, 54:61–69. The underlying chronic immune response can be characterized by four important histopathological events, which predominantly occur within the first three months after transplantation: 1) invasion of the adventitia by inflammatory cells; 2) disappearance of all medial smooth muscle cells, suggesting a relationship between smooth muscle cell antigenicity and the rejection process; 3) matrix degeneration; and 4) intimal hyperplasia. Experimentally, the rejection process is self-limited for approximately 100 days. Todd I A and Boctor Z N, Experimental homotransplantation of arteries, Transplantation. 1966, 4:123–130. The graft performance is then determined by the thrombogenicity of the luminal surface and the mechanical strength of the remodeled arterial scaffold.

To date, two avenues have been followed to overcome immunological rejection in transplanted blood vessels: attenuation of immune responses in the host through immunosuppressive drugs (Schmitz-Rixen T, Megerman J, Colvin R B, Williams A M, Abbott W M, Immunosuppressive treatment of aortic allografts, J Vasc Surg. 1988, 7:82–92; Steele D M, Hullett D A, Bechstein, Kowalski J, Smith L S, Kennedy E, Allison A C, Sollinger H W, Effects of immunosuppressive therapy on the rat aortic allograft model, Transplant Proc. 1993, 25:755–756; DaGama A D, Sarmento C, Vieira T, do Carmo G X, The use of arterial allografts for vascular reconstruction in patients receiving immunosuppression for organ transplantation, J Vasc Surg. 1994, 20:271–278) and reduction of graft antigenicity using different preservation and preparation techniques. Rosenberg N, The bovine arterial graft and its applications, Surg Gynecol Obstet. 1976, 142:104–108; Boren C H, Roon A J, Moore W S, Maintenance of viable arterial allografts by cryopreservation, Surgery. 1977, 83:382–391; Sitzman J V, Imbembo A I, Ricotta J J, et al., Dimethyl sulfoxide treated cryopreserved venous allografts in the arterial and venous systems, Surgery. 1984, 95:154–159; Dumont C E, Plissonier D, Guettier C, Michel J B, Effects of glutaraldehyde on experimental arterial iso- and allografts in rats, J Surg Res. 1993, 54:61–69; Marin M L, Hardy M A, Gordon R E, Reemtsma K, Benvenisty A I, Immunomodulation of vascular endothelium: effects of ultraviolet B irradiation on vein allograft rejection, J Vasc Surg. 1990, 11:103–111.

Clinical trials applying these approaches have yet to demonstrate an unequivocal reduction in the incidence of rejection. The use of immunosuppressants like cyclosporine may considerably reduce leukocyte infiltration or delay the development of intimal hyperplasia, but cannot entirely suppress the rejection process. Schmitz-Rixen T, Megerman J, Colvin R B, Williams A M, Abbott W M, Immunosuppressive treatment of aortic allografts, J Vasc Surg. 1988, 7:82–92; Steele D M, Hullett D A, Bechstein, Kowalski J, Smith L S, Kennedy E, Allison A C, Sollinger H W, Effects of immunosuppressive therapy on the rat aortic allograft model, Transplant Proc. 1993, 25:755–756. These drugs also pose additional risks and side-effects, and are often poorly tolerated by polymorbid patients. DaGama A D, Sarmento C, Vieira T, do Carmo G X, The use of arterial allografts for vascular reconstruction in patients receiving immunosuppression for organ transplantation, J Vasc Surg. 1994, 20:271–278. Cryopreservation, using liquid nitrogen vapor in conjunction with dimethyl sulfoxide, is currently a favored method of maintaining viability and structural integrity of vascular grafts. Boren C H, Roon A J, Moore W S, Maintenance of viable arterial allografts by cryopreservation, Surgery. 1977, 83:382–391; Sitzman J V, Imbembo A I, Ricotta J J, et al., Dimethyl sulfoxide treated cryopreserved venous allografts in the arterial and venous systems, Surgery. 1984, 95:154–159. Nevertheless, significant antigenicity of cryopreserved veins and arteries still represents a major obstacle to their widespread use. Perloff L J, Rowlands D T, Barker C F, Studies of the modified venous allograft, Ann Surg. 1977, 1986:227–232. Application of fixatives like glutaraldehyde appears to induce nonspecific inflammatory responses in the adventitia and structural degradation and calcification of the graft. Additional crosslinking of extracellular matrix proteins leads to anastomotic compliance mismatch, and subsequent intimal hyperplasia. Dumont C E, Plissonier D, Guettier C, Michel J B, Effects of glutaraldehyde on experimental arterial iso- and allografts in rats, J Surg Res. 1993, 54:61–69. Moreover, fixatives have not been able to uniformly penetrate the full thickness of the arterial wall, resulting in "incomplete" graft preservation. Dumont C E, Plissonier D, Guettier C, Michel J B, Effects of glutaraldehyde on experimental arterial iso- and allografts in rats, J Surg Res. 1993, 54:61–69.

Another approach is decellularization of arterial allo- and xenografts, induced by the detergent sodium dodecyl sulfate. Allaire E, Guettier C, Bruneval P, Plissonier D, Michel J B, Cell-free arterial grafts: Morphologic characteristics of aortic isografts, allografts and xenografts in rats, J Vasc Surg. 1994, 19:446–456. This treatment reduced the immune injury with preservation of medial elastin in the presence of very few adventitial inflammatory cells. The presence of inflammatory cells, despite complete decellularization, was attributed to minor antigenicity of extracellular matrix components, not targeted by the detergent.

In previous vascular PDT studies, the photosensitizer CASPc was shown to possess advantageous properties. Ortu P, LaMuraglia G M, Roberts G W, Flotte T J, Hasan T, Photodynamic therapy of arteries. A novel approach for treatment of experimental intimal hyperplasia, Circulation. 1992, 3:1189–1196; Grant W E, Speight P M, MacRobert A J, Hopper C, Bown S G, Photodynamic therapy of normal rat arteries after photosensitization using disulphonated aluminum phthalocyanine and 5-aminolaevulinic acid, Br J Cancer. 1994, 70:72–78; LaMuraglia G M, Ortu P, Flotte T J, Roberts W G, Schomacker K T, ChandraSekar N R, Hasan T, Chloroaluminum sulfonated phthalocyanine partioning in normal and intimal hyperplastic artery in the rat. Implications for photodynamic therapy, Am J Pathol. 1993, 142:1898–1905.

MHC antigens in endothelial and medial smooth muscle cells are the primary targets of the rejection process in vascular grafts. Mennander A, Tiisala S, Halttunen J, Yilmaz S, Paavonen T, Havry P, Chronic rejection in rat aortic allografts: an experimental model for transplant arteriosclerosis, Arterioscler Thromb. 1991, 11:671–680. Removal of the graft from the donor and acute rejection are responsible for the rapid destruction of the blood vessel endothelium. Mennander A, Tiisala S, Halttunen J, Yilmaz S, Paavonen T, Havry P, Chronic rejection in rat aortic allografts: an experimental model for transplant arteriosclerosis, Arterioscler Thromb. 1991, 11:671–680; Galumbeck M A, Sanfilippo F P, Hagen P O, Seaber A V, Urbaniak J R, Inhibition of vessel allograft rejection by endothelial removal, Ann Surg. 1987, 206:757–764. Hence, the remaining smooth muscle cells are the principal sites of chronic rejection in transplanted arteries. Dumont C E, Plissonier D, Guettier C, Michel J B, Effects of glutaraldehyde on experimental arterial iso- and allografts in rats, J Surg Res. 1993, 54:61–69.

Autologous veins and textile manufactured polymeric grafts play a fundamental role in the treatment of peripheral and coronary vascular disease. Nevertheless, synthetic prostheses yield a relatively low patency rate as replacement for small diameter arteries (<6 mm) compared with autologous veins and therefore cannot be considered applicable as grafts for, e.g., coronary artery bypass surgery. On the other hand, autologous veins may be unavailable or physically unsuitable in 8.5 to 35% of patients (Bosher L P: Fresh and preserved homograft vein as a vascular conduit. In: Wright C B, ed. Vascular grafting: clinical applications and techniques. Boston, Mass. John Wright; 1983) because of previous use, degeneration, or absence (e.g., after vein stripping).

Transplanted arteries have been part of the vascular surgeon's armamentarium for generations. Some of the earliest work in vascular reconstruction used tissue of both human and nonhuman origin. Carrel A, Heterotransplantation of blood vessels preserved in cold storage, J Exp Med. 1907, 9:226–228; Guthrie C C, Structural changes and survival of cells in transplanted blood vessels, J Am Med Assoc. 1908, 50:1035–1036. Bovine heterografts (Rosenberg N, The bovine arterial graft and its applications, Surg Gynecol Obstet. 1976, 142:104–108) and cryopreserved human arterial and venous allografts (Boren C H, Roon A J, Moore W S, Maintenance of viable arterial allografts by cryopreservation, Surgery 1977, 83:382–391; Sitzman J V, Imbembo A I, Ricotta J J, et al., Dimethyl sulfoxide treated cryopreserved venous allografts in the arterial and venous systems, Surgery 1984, 95:154–159) have been tested as arterial bypass conduits. However, studies on arterial allografts revealed significant histological changes due to chronic rejection. Mennander A, Tiisala S, Halttunen J, Yilmaz S, Paavonen T, Hävry P, Chronic rejection in rat aortic allografts: an experimental model for transplant arteriosclerosis, Arterioscler Thromb. 1991, 11:671–680; Todd I A and Boctor Z N, Experimental homotransplantation of arteries, Transplantation. 1966, 4:123–130. Shortly after implantation, infiltration of T-cells and macrophages causes a severe inflammatory reaction with breakdown and degeneration of the collagen-elastin network in the media. This event can result in a loss of biomechanical stability with graft dilatation, aneurysm formation and rupture. Furthermore, endothelial cell damage and later myointimal proliferation may lead to thrombus formation, anastomotic narrowing and graft occlusion.

Problems relating to the elimination of vessel graft antigens and preservation of vessel function are not as complex as those involved in organ transplantation. Viability of the implanted graft, while possibly desirable, is not a principal requirement. Therefore, vascular grafts of biological origin have been subjected to a wide variety of preservation techniques before implantation. These techniques included a large number of preservation or preparation procedures such as chemical stabilization (Dumont C E, Plissonier D, Guettier C, Michel J B, Effects of Glutaraldehyde on experimental arterial iso- and allografts in rats, J Surg Res. 1993, 54:61–69), cryopreservation, lyophilization, UV (Marin M L, Hardy M A, Gordon R E, Reemtsma K, Benvenisty A I, Immunomodulation of vascular endothelium: effects of ultraviolet B irradiation on vein allograft rejection, J Vasc Surg. 1990, 11:103–111) and gamma irradiation.

Photodynamic therapy (PDT) is a process utilizing light to activate otherwise relatively inert photosensitizers (PS) for the production of activated free-radical moieties. Following absorption of light, the PS is transformed into an excited triplet state from where it can either directly form a free radical (Type I reaction) or transfer its energy to oxygen to form an oxygen radical which can also cause cell injury (Type II reaction). These free radicals exert cytotoxic effects by damaging cellular membranes and organelles as well as crosslinking proteins. Henderson B W and Dougherty T J, Photochem Photobiol. 1991, 55:145–157; Verweij H, Dubbelman T M A R, Van Stevenick J., Biochim Biophys Acta. 1981, 647:87–94.

In experimental studies, PDT has been shown to inhibit hyperplasia by cell depletion of the vessel wall, without provoking an inflammatory response. Ortu P, LaMuraglia G M, Roberts G W, Flotte T J, Hasan T, Photodynamic Therapy of Arteries: A Novel Approach for Treatment of Experimental Intimal Hyperplasia, Circulation. 1992, 3:1189–1196; Grant W E, Speight P M, MacRobert A J, Hopper C, Bown S G, Br J Cancer. 1994, 70:72–78.

SUMMARY OF THE INVENTION

The present invention uses photodynamic therapy (PDT), a technique to produce cytotoxic free radicals, as a method for preparing arterial allografts. It has been found that a graft is rendered less susceptible to host rejection when the graft is contacted with a photosensitizing compound and then exposed to electromagnetic radiation, preferably visible or UV light, to destroy rejection-inducing cells in the graft.

Accordingly, the invention features treating a graft, e.g., an allograft or xenograft, preferably an arterial allograft, to reduce or inhibit rejection. The graft is contacted with a photosensitizing compound and then exposed to electromagnetic radiation to kill cells in the graft.

Grafts treated using the method of the invention should have an extracellular matrix such as collagen fibers, reticular fibers, or elastic fibers, and an amorphous ground substance of proteoglycans and glycosaminoglycans. Treatment of the graft according to the invention causes the death of cells (such as endothelial cells, smooth muscle cells, fibroblasts, histiocytes, osteoblasts, osteoclasts, chondroblasts, chondroclasts, and white blood cells) of the graft. Because the cells of the graft have major histocompatibility complex antigens on their surfaces, the death of these cells removes an initiator of a host rejection reaction. The photodynamic therapy of the invention may also alter other biological molecules in the matrix and the cells, altering the host's ability to mount an unwanted immune response. The extracellular matrix is necessary to maintain the structure of the graft treated using the method of the invention. The structure provided by the extracellular matrix may become repopulated by the cells of the host following transplantation.

Tissues that may be used as grafts in the invention include, but are not limited to, elastic muscular artery or vein, cardiac valve, capsular tissue, tendon, cartilaginous tissue, bone, skin, intraocular lens, and corneal tissue.

Photosensitizing compounds that may be used in the invention include, but are not limited to, chloroaluminum phthalocyanine of mono, di, tri, tetra, or mixed sulfonation, bacteriochlorophyll a, benzoporphyrin derivative-monoacid, mono-L-aspartyl chlorin e6, N'-bis(2ethyl-1,3-dioxolane) kryptocyanine, and Photofrin II. The choice of the photosensitizing compound determines the wavelength of the electromagnetic radiation employed. Electromagnetic radiation that may be used in the invention includes, but is not limited to, light, e.g., of wavelengths between 190–800 nm and delivered with a total fluence of, e.g., 1–1000 J/cm$^2$. Wavelength and total fluence will vary with the amount and efficiency of the photosensitizing compound used. If a laser is used as a light source, irradiance can vary widely; in some cases, irradiance of less than 200 mw/cm$^2$ can be used. Alternatively, if heating is desired, higher values will be used. One embodiment employs coherent laser light of a wavelength of 675 nm, magnified to provide a uniform 2 cm spot, calibrated to an irradiance of 100 mW/cm$^2$, and delivered with a total fluence of 100 J/cm$^2$.

The invention can be used in conjunction with either an allograft, which is a graft transplanted between genetically nonidentical individuals of the same species, or a xenograft, which is a graft transplanted from an animal of one species to one of another species.

Other features and advantages of the invention will be apparent from the following detailed description thereof, and from the claims.

DETAILED DESCRIPTION

Photodynamic therapy can be considered as a specialized and targeted form of chemotherapy, in which the drug itself is essentially harmless unless activated by exposure to wavelength-specific light. Alternatively, PDT may also be considered an extension of radiotherapy where, because of prior sensitization of the tissue, cytotoxicity is induced at lower radiation energies than with conventional radiotherapy. Similar to ionizing radiation, the PDT-effect occurs within a short time frame and is localized to the irradiated field. PDT therefore appears to be highly suitable for ex vivo or in vivo treatment prior to graft utilization.

In the case of xenografts, one or multiple in vivo PDT treatments may be carried out prior to removal of the graft from the donor; after these steps, further PDT treatment can be carried out prior to graft utilization, or the graft can be utilized immediately, or kept under storage conditions for use at a later time. In addition, the PDT method of the invention can be used in conjunction with other preparation treatment procedures such as perfusion with solutions which mask or eliminate antigens, or alter the biological properties of the matrix. Another alternative is to treat a graft after it has been engrafted into the recipient patient; this can be done after the graft has first been treated ex vivo, or the treatment can occur for the first time in the recipient. This in vivo treatment may also provide a second benefit, which is an immunosuppression reaction which further inhibits rejection. In addition, in vivo treatments can be carried out as part of the recipient follow-up work, e.g., when a vascular graft develops, in the region of the graft, intimal hyperplasia, a subsequent treatment can be performed locally.

In the experiments described above, donor animals were injected with CASPc 24 hours prior to harvest, when they are known to have elevated PS concentrations in the vessel wall. LaMuraglia G M, Ortu P, Flotte T J, Roberts W G, Schomacker K T, ChandraSekar N R, Hasan T, Chloroaluminum sulfonated phthalocyanine partioning in normal and intimal hyperplastic artery in the rat. Implications for photodynamic therapy, Am J Pathol. 1993, 142:1898–1905. PDT-treated allografts which were harvested 24 hours after transplantation displayed complete decellularization of the artery. However, preincubation with the photosensitizer should be effective at other times.

PDT, according to the invention brought about depletion of all cells in the vessel wall, and therefore potential major histocompatibility antigen bearing targets were not present after implantation. It can therefore be inferred that infiltration of mononuclear cells, which would have indicated an ongoing rejection process, was prevented as a consequence of total smooth muscle cell eradication after PDT. Nevertheless, at 8 weeks a small number of polymorphonuclear cells persisted in the adventitia of PDT grafts. It can be hypothesized that antigens in the extracellular matrix, which had not been targeted by the PDT treatment, may have contributed to this inflammatory response. Allaire E, Guettier C, Bruneval P, Plissonier D, Michel J B, Cell-free arterial grafts: Morphologic characteristics of aortic isografts, allografts and xenografts in rats, J Vasc Surg. 1994, 19:446–456. Antigenic presentation may also have played a role; attenuated antigens in the blood of the host may have perfused out of the transplanted artery, causing rejection.

The structural integrity of the elastic laminae in PDT-grafts remained intact at all time points, whereas untreated allografts demonstrated focal fragmentation. Although medial thickness in PDT and control allografts was equivalent, significant graft dilatation was seen only in control allografts. These data confirm previous findings, which acknowledge the importance of mechanical stress to a thinner arterial wall, but attribute aneurysmal dilatation primarily to immunologically induced destruction of medial elastin. Allaire E, Guettier C, Bruneval P, Plissonier D, Michel J B, Cell-free arterial grafts: Morphologic characteristics of aortic isografts, allografts and xenografts in rats, J Vasc Surg. 1994, 19:446–456. Moreover, other studies on the effect of elastase and concomitant inflammation verified temporal correlation between inflammatory infiltrate, destruction of elastic laminae and dilatation. Anidjar S, Salzmann J L, Gentric D, Lagneau P, Camilleri P, Michel J B, Elastase-induced experimental aneurysms in rats, Circulation. 1990, 82:973–81; Anidjar S, Dobrin P B, Eichorst M, Graham G P, Chejfec G, Correlation of inflammatory infiltrate with the enlargement of experimental aortic aneurysms, J Vasc Surg. 1992, 16:139–147. Nevertheless, at 8 weeks external diameters of PDT grafts increased by approximately 13%, whereas isografts remained almost unchanged. Although it cannot be ruled out that graft dilatation after PDT may have occurred on the basis of an insidious rejection process, previous studies corroborate intrinsic, PDT-induced diameter increases. L'Italien G J, Chandrasekar N R, LaMuraglia G M, Pevec W C, Dhara S, Warnock D F, Abbott W M, Biaxial elastic properties of rat arteries in vivo: influence of vascular wall cells and anisotropy, Am J Physiol. 1994, 267:H574–H579. By maintaining a "crimp" geometry of elastic fibers, smooth muscle cells reduce direct stresses on similarly aligned collagen. When smooth muscle cell tone is eliminated (e.g. after PDT treatment), the vessel diameter increases, stiffer collagen fibers are directly stressed, and circumferential compliance is reduced.

In the present study, the area of IH in PDT-allografts at 2 weeks was significantly less compared to LO, and at 4 weeks equivalent to ISO and LO. At 8 weeks, however, IH in PDT grafts, though almost unchanged to 4 weeks, was increased as compared to ISO. A possible compliance mismatch between graft and adjacent arterial segments, due to the loss of smooth muscle cell tone (L'Italien G J, Chandrasekar N R, LaMuraglia G M, Pevec W C, Dhara S, Warnock D F, Abbott W M, Biaxial elastic properties of rat arteries in vivo: influence of vascular wall cells and anisotropy, Am J Physiol. 1994, 267:H574–H579) and increased structural compactness of adventitial collagen after photodynamic therapy (LaMuraglia G M, ChandraSekar N R, Flotte T J, Abbott W M, Michaud N, Hasan T, Photodynamic therapy inhibition of experimental intimal hyperplasia: Acute and chronic effects, J Vasc Surg. 1994, 19321–331) may be contributory to the comparably larger intimal areas in PDT-grafts by 8 weeks. The degree of compliance mismatch present in the graft body affects the amount of intimal hyperplasia that develops. Abbott W M, Megerman J, Hasson J E, L'Italien G, Warnock D F, Effect of compliance mismatch on vascular graft patency, J Vasc Surg. 1987, 5:376–382. Although compliance of the allografts was not evaluated, the inferred compliance differences may explain the development of moderate IH in PDT grafts.

As indicated by scanning electron microscopy, the luminal surface of PDT grafts was completely reendothelialized at 4 weeks. This finding suggests that PDT provides a non-thrombogenic luminal surface, which allows attachment and migration of repopulating endothelial cells and may help diminish subsequent development of IH. The resulting decellularized graft, lined by endothelial cells which should minimize thrombus formation, represents a prerequisite for satisfactory long-term graft performance. Non-treated control allografts which present with no coherent endothelial cell lining, but significant adhesion of platelets, are most likely prone to thrombus formation, intimal hyperplasia, and finally graft failure.

In conclusion, photodynamic therapy pre-treatment of allografts quantitatively suppressed histological markers of arterial wall immune injury: adventitial inflammation, aneurysmal dilatation and the development of intimal hyperplasia. PDT appears to be a safe method of producing a biocompatible and non-thrombogenic arterial scaffold for use as a bypass graft.

EXAMPLE 1

Preparation of Biologic Grafts Using Photochemistry

Summary of Exmerimental Results

The work described below was undertaken to investigate the effects of PDT on graft rejection in an allotransplantation model using rats of two histocompatibly disparate, high-responder, inbred strains.

Aortas of ACI rats were impregnated with the photosensitizer chloroaluminum sulfonated phthalocyanine and then treated with 675 nm light prior to orthotopic transplantation in Lewis rats (PDT). Controls included nontreated (NT), photosensitizer only (PO) and light irradiation only (LO) allografts. Lewis-to-Lewis isotransplants (ISO) served as negative control. PDT, LO and ISO were sequentially analyzed at 2, 4, and 8 weeks by morphometry and immunohistochemistry. PO and NT were examined at 8 weeks only.

No histological or morphometrical differences were observed between NT, PO and LO. NT and LO developed 4/25 (16%) aneurysms, compared to 0/33 in PDT or ISO ($p<0.001$). PDT-treatment of allografts significantly inhibited intimal hyperplasia ($p<0.001$) and resulted in intimal areas comparable to ISO. Medial thickness in both LO and PDT grafts was markedly decreased as compared to isografts. External graft diameters at 8 weeks in NT, PO and LO were significantly enlarged ($p<0.02$). At all time points, immunohistochemically verified T-lymphocytes were found in a substantially larger number in LO, than in PDT or ISO. Scanning electron microscopy at 4 weeks confirmed complete repopulation with endothelial cells in PDT, which was not seen in LO.

All animals appeared healthy, without evidence of weight loss during the study. No skin photosensitivity was noted in the animals exposed to CASPc. All grafts were patent at harvest. Measured mid-graft-diameter values were corrected for animal-growth. At harvest, one untreated (NT) and three grafts from group LO (16%) were noted to have aneurysmal degeneration ($p<0.001$), defined as diameter increase greater 2.5 times of the baseline diameter. No aneurysms were seen in PDT or ISO. Macroscopically, there was evidence of perigraft inflammation with scarring in all control allografts, predominantly at 4 and 8 weeks. At harvest, PDT treated allografts seemed to have thinner vessel walls with a transparent appearing bluish hue as compared to ISO, whose grafts appeared unchanged.

Experimental Design

Inbred ACI ($RT1^a$) and Lewis, i.e., LEW, ($RT1^1$) rats (Harlan Sprague Dawley, Indianapolis, Ind. and Charles River Breeding Laboratories, Wilmington, Mass.), weighing 270±60 g, were used as the respective donor and recipient. The animals were anesthetized with intramuscular Ketamine (75 mg/kg) and Xylazine (5 mg/kg). After intravenous injection of 200 U/kg Heparin, a segment of infrarenal aorta was resected, and thoroughly rinsed with saline before use. All side branches in this segment were ligated, and a 1 cm graft was orthotopically implanted with interrupted 9–0 nylon sutures (Ethicon Inc., Somerville, N.J.). Surgery was performed under 10–20×magnification with an operating microscope (Edward Weck & Company, Triangle Park, N.C.). For all grafts, total ischemia time was approximately 50 minutes during which the graft was kept in 4° C. Hanks buffered salt solution. Subcutaneous Butorphanol (1 mg/kg) was administered for postoperative analgesia. Graft patency was evaluated by daily palpation of both femoral pulses and verified at harvest. While maintained in a standard 12-hour light/dark cycle, the animals had free access to standard rat chow (Purina rat chow 5001, Ralston Purina, St. Louis, Mo.) and water. Animal care was in strict compliance with "Principles of Laboratory Animal Care" and the "Guide for the Care and Use of Laboratory Animals" (NIH Publication No. 80-23, Revised 1985). All procedures were also approved by an independent institutional animal care committee.

The animals were assigned to five different experimental groups: in the treatment group, PDT-treated ACI aortas were grafted in LEW rats (PDT). As controls, non PS-impregnated, but irradiated ACI-grafts (LO), PS-impregnated, non-irradiated (PO) and non PS-impregnated, non irradiated allografts (NT) were studied. Syngeneic isotransplantations of untreated aortic grafts (ISO) were made from LEW to LEW rats, verified surgical changes and served as negative control for the transplantation model. Animals from every group, except NT and PO, were sacrificed sequentially at 2, 4 and 8 weeks. To minimize the number of animals, NT and PO rats were studied only at 8 weeks. For the whole study 59 transplantations were performed.

Photodynamic Therapy

The photosensitizer chloroaluminum sulfonated phthalocyanine (CASPc, Ciba Geigy, Basel, Switzerland) was diluted to a concentration of 5 mg/ml in phosphate-buffered saline solution (PBS) and administered intravenously at a dose of 5 mg/kg, 24 hours prior to explantation of PDT and PO grafts. Animals of groups ISO, LO and NT received an equivalent volume of saline solution. Rats receiving the PS without pre-implantation laser irradiation (PO) had the aorta resected in low ambient light. Implantation of these grafts was performed under filtered illumination at a bandpass of 440–600 nm to avoid photoactivation of CASPc, already present in the tissue of the allograft.

For irradiation of PDT and LO grafts, an Argon-pumped dye laser (Coherent INNOVA I 100 and Coherent CR 599, Coherent, Palo Alto, Calif.) was tuned to emit light at 675 nm, which was coupled to a 1 mm core, silica fiber. With a 5 mm focal-length lens the output from the fiberoptic was magnified to provide a uniform 2 cm spot and calibrated to an irradiance of 100 mW/cm$^2$. The grafts were placed on a reflective surface in a Petri dish, which contained 5 $\mu$g/ml CASPc in PBS, and were subsequently irradiated to deliver a fluence rate of 100 J/cm$^2$. After gentle rinsing with PBS, the aortic grafts were stored in 4° C. Hanks solution prior to implantation.

Harvest

Under anesthesia, the iliac artery was cannulated for blood pressure monitoring and perfusion fixation. Mid-graft diameters were determined in the donor animal prior to explanation, and in the recipient before euthanasia using a calibrated eyepiece in the operating microscope. After euthanasia, the aorta was flushed with saline and subsequently in situ perfusion-fixed at 80 mm Hg with 10% buffered formalin for light microscopy or 1.5% glutaraldehyde in cacodylate buffer for electron microscopy. The grafts were excised and placed in fresh 10% formalin or 4% glutaraldehyde respectively. For immunohistochemistry fresh grafts were excised, thoroughly saline rinsed and placed in Tissue tek O.C.T. compound® (Miles Inc. Elkhart, Ind.) prior to storage at –70° C.

Morphological and Immunohistochemical Studies

Formalin-fixed sections from three different graft segments (proximal, mid, distal) were prepared with hematoxylin-eosin and Verhoeff's elastin stain. Morphometric evaluation was performed using a digitizing measurement system (Sigma Scan, Jandel Scientific, Sausalito, Calif.) coupled to a camera lucida. Ortu P, LaMuraglia G M, Roberts G W, Flotte T J, Hasan T, Photodynamic therapy of arteries. A novel approach for treatment of experimental intimal hyperplasia, Circulation. 1992, 3:1189–1196. The inflammatory response was assessed by scoring for cellular infiltration at 400×magnification using the following arbitrary score: 0(<5 cells/field); 1(5–25 cells/field); and 2(>25 cells/field).

Monoclonal anti-rat OX 47 antibody against T-lymphocytes (Sera Lab, Sussex, England) was used for immunohistochemical characterization of the inflammatory infiltrates. Four micron cryosections were stained using the two-layer indirect immunoperoxidase technique. Mennander A, Tiisala S, Halttunen J, Yilmaz S, Paavonen T, Hävry P, Chronic rejection in rat aortic allografts: an experimental model for transplant arteriosclerosis, Arterioscler Thromb. 1991, 11:671–680. Briefly, the sections were air dried for 30 minutes and subsequently fixed in acetone for 8 minutes. After incubation with primary antibody (1:1000), endogenous peroxidase activity was blocked with 0.3% $H_2O_2$ in PBS. Following incubation with normal horse serum and rat adsorbed, biotinylated horse anti-mouse immunoglobulin (Vector Laboratories, Burlingame, Calif.), treatment with diaminobenzidine (DAB substrate Kit, Vector, Burlingame, Calif.) and counterstain with Nuclear Fast Red (Sigma Chemical Co., St. Louis, Mo.) were performed. Normal arteries were used as negative controls and thymus tissue was used as positive control.

Data are expressed as means ±SEM. An analysis of variance (ANOVA) with Bonferoni correction was used to compare morphometric parameters of the three non-treated allograft controls NT, LO and PO. The inflammatory scores were analyzed with the Chi-square-test. Statistical analysis of the morphohistometric data was performed with a two tailed Student's t-test; p-values of less than 0.05 were considered to be significant.

No histological differences were observed between allografts of groups NT, LO and PO. Peaking at 4 weeks, LO grafts displayed a large number of lymphocytes infiltrating the adventitia and to a lesser degree media and intima (FIG. 1), which demonstrated positive labeling with the monoclonal antibody OX 47 to T-Cells. At 2 and 4 weeks, an infiltration of white blood cells was also observed in both PDT treated allografts and isografts. Unlike NT, LO and PO, however, the infiltrate in PDT and ISO consisted primarily of polymorphonuclear cells. At 8 weeks, this infiltrate was persisting in the adventitia of PDT allografts, whereas isografts presented without any significant inflammation at this time point. All examined grafts presented with no statistically significant difference between the numbers of inflammatory cells in the proximal, mid or distal graft segments.

Inflammatory degeneration of the media with fragmentation of the internal elastic lamina was noted at 2 weeks and was highest at 8 weeks in LO grafts. Elastic laminae were no longer in parallel orientation, and the space between the laminae was widened. Regardless of treatment or the time interval, all allografts demonstrated thinner medial layers than their respective isograft counterparts. Smooth muscle cells in the media of LO grafts diminished over time and were almost undetectable by 8 weeks. In PDT grafts, however, smooth muscle cells were entirely eliminated from the media and could not be seen at any time. The media appeared to be compacted and acellular. An amorphous eosinophilic material was observed between the elastic laminae, and the internal elastic lamina remained intact. Although medial areas of non-PDT and PDT allografts were equivalent at 8 weeks, external diameters of non-PDT grafts increased significantly by approximately 47% versus 13% in PDT allografts ($p<0.02$). In contrast, medial smooth muscle cells appeared to be viable in syngeneic controls, and medial areas as well as external diameters remained almost unchanged.

Intimal hyperplasia was present in LO grafts at all time intervals, often unevenly distributed and mostly confined to graft segments near the proximal and the distal anastomoses. The IH was hypercellular at 2 and 4 weeks, while by 8 weeks it was less cellular and contained mostly extracellular matrix. At 8 weeks the intimal area was notably increased in LO with $0.23\pm0.02$ mm$^2$ versus $0.09\pm0.02$ mm$^2$ in PDT and ISO $0.06\pm0.03$ mm$^2$ ($p<0.001$). No significant IH was seen in PDT grafts at 2 and 4 weeks.

Scanning Electron Microscopy

To determine differences in endothelialization and structure of the intimal surface between PDT and untreated allografts, scanning electron microscopy of longitudinal sections was performed at 4 weeks. After overnight fixation in buffered 4% glutaraldehyde, the specimens were dehydrated in increasing concentrations of ethanol. Then, after critical point drying and coating with a thin film of gold palladium, the sections were examined with a scanning electron microscope (Amray 1400, Amray, Bedford, Mass.).

Scanning electron microscopy at 4 weeks was used to examine endothelial morphology, and repopulation of the luminal surfaces in PDT-treated and non-treated allografts. PDT-treated allografts demonstrated complete covering with normal appearing endothelial cells, whereas non-treated allografts presented with abundant platelets and rare erythrocytes adhering to denuded luminal surfaces.

OTHER EMBODIMENTS

Other embodiments are within the following claims.

What is claimed is:

1. A method for reducing host rejection of a biologic graft, said method comprising the steps of:

(a) contacting a tissue graft with a photosensitizing compound, and (b) exposing said graft to electromagnetic radiation for a predetermined time and in an amount effective to transform the photosensitizing compound into an excited state, wherein said exposure results in the activation of the photosensitizing compound to produce an activated free-radical moiety which causes the death of rejection-inducing cells of the graft.

2. The method of claim 1, wherein said graft comprises an extracellular matrix and an amorphous ground substance comprising at least one proteoglycan or glycosaminoglycan.

3. The method of claim 1, wherein said photosensitizing compound is a sulfonated chloroaluminum phthalocyanine, bacteriochlorophyll a, benzophorphyrin derivative-monoacid, mono-L-aspartyl chlorine 6, N'-bis(2-ethyl-1,3-dioxolane)kryptocyanine, or dihematoporphyrin ether.

4. The method of claim 1, wherein the wavelength of said electromagnetic radiation is between 180 and 800 nanometers.

5. The method of claim 1, wherein said graft is an allograft or xenograft.

6. The method of claim 1, wherein said graft is selected from the group consisting of artery, vein, cardiac valve, capsular tissue, tendon, ligament, cartilaginous tissue, bone, skin, intraocular lens, corneal tissue, vascular tissue, and cardiac tissue.

7. The method of claim 6, wherein said graft is an artery or vein.

* * * * *

UNITED STATES PATENT AND TRADEMARK OFFICE
CERTIFICATE OF CORRECTION

| | | |
|---|---|---|
| PATENT NO. | : 5,824,080 | Page 1 of 1 |
| APPLICATION NO. | : 08/708376 | |
| DATED | : October 20, 1998 | |
| INVENTOR(S) | : Glenn M. Lamuraglia | |

It is certified that error appears in the above-identified patent and that said Letters Patent is hereby corrected as shown below:

Column 1, after line 24, add --This invention was made with Government support under Grant No. N00014-91-C-0084 awarded by the U.S. Department of the Navy. The Government has certain rights in this invention.--

Signed and Sealed this

Seventh Day of July, 2009

JOHN DOLL
*Acting Director of the United States Patent and Trademark Office*